(12) United States Patent
Johns et al.

(10) Patent No.: US 11,957,820 B2
(45) Date of Patent: Apr. 16, 2024

(54) BLOOD PUMP

(71) Applicant: Haemaflow Limited, Swansea (GB)

(72) Inventors: William Richard Johns, Swansea (GB); Ronald Kelvin Knight, Swansea (GB)

(73) Assignee: Haemaflow Limited, Swansea (GB)

( * ) Notice: Subject to any disclaimer, the term of this patent is extended or adjusted under 35 U.S.C. 154(b) by 733 days.

(21) Appl. No.: 16/332,776

(22) PCT Filed: Sep. 14, 2017

(86) PCT No.: PCT/GB2017/052706
§ 371 (c)(1),
(2) Date: Mar. 12, 2019

(87) PCT Pub. No.: WO2018/051091
PCT Pub. Date: Mar. 22, 2018

(65) Prior Publication Data
US 2019/0358375 A1 Nov. 28, 2019

(30) Foreign Application Priority Data
Sep. 14, 2016 (GB) .................................... 1615650

(51) Int. Cl.
*A61M 1/16* (2006.01)
*A61M 1/36* (2006.01)
(Continued)

(52) U.S. Cl.
CPC ........ *A61M 1/1698* (2013.01); *A61M 1/3667* (2014.02); *A61M 39/24* (2013.01);
(Continued)

(58) Field of Classification Search
CPC .. A61M 1/3667; A61M 1/1698; A61M 39/24; A61M 2039/244; A61M 2039/248;
(Continued)

(56) References Cited

U.S. PATENT DOCUMENTS

| 3,656,873 A | 4/1972 | Schiff |
| 3,955,557 A * | 5/1976 | Takagi ................. A61M 60/40 |
| | | 417/244 |

(Continued)

FOREIGN PATENT DOCUMENTS

| KR | 20100137116 A | 12/2010 |
| WO | 8910763 | 11/1989 |

(Continued)

OTHER PUBLICATIONS

International Preliminary Report on Patentability for corresponding PCT Application No. PCT/GB2017/052706, dated Mar. 28, 2019, 9 pgs.

(Continued)

*Primary Examiner* — Philip R Wiest
(74) *Attorney, Agent, or Firm* — Shumaker & Sieffert, P.A.

(57) ABSTRACT

A blood pump is disclosed. The blood pump apparatus is arranged to provide pulsatile flow, and comprises a flexible inner cylindrical duct providing a blood flow region, and an outer cylindrical duct arranged to surround the inner cylindrical duct and arranged to accommodate a pumping fluid. In the pump the inner cylindrical duct is described as comprising a blood inlet for receiving blood into the region, a blood outlet for passing blood out from the blood flow region and a passageway therebetween. There is also described the feature of the inner duct comprising a non return valve at the blood inlet and a non return valve at the blood outlet, the outer cylindrical duct having a fluid port for a pumping fluid, and a pump device arranged to cyclically deliver and withdraw pumping fluid to the fluid port thereby cyclically compressing and expanding the flexible inner cylindrical duct urging blood through the blood flow region (Continued)

and delivering a pulsating blood flow through the blood outlet.

15 Claims, 6 Drawing Sheets

(51) Int. Cl.

| | | |
|---|---|---|
| *A61M 39/24* | (2006.01) |
| *A61M 60/113* | (2021.01) |
| *A61M 60/258* | (2021.01) |
| *A61M 60/268* | (2021.01) |
| *A61M 60/284* | (2021.01) |
| *A61M 60/38* | (2021.01) |
| *A61M 60/441* | (2021.01) |
| *A61M 60/562* | (2021.01) |
| *A61M 60/849* | (2021.01) |
| *A61M 60/851* | (2021.01) |
| *A61M 60/892* | (2021.01) |

(52) U.S. Cl.
CPC ........ *A61M 60/113* (2021.01); *A61M 60/258* (2021.01); *A61M 60/268* (2021.01); *A61M 60/284* (2021.01); *A61M 60/38* (2021.01); *A61M 60/441* (2021.01); *A61M 60/562* (2021.01); *A61M 60/849* (2021.01); *A61M 60/851* (2021.01); *A61M 60/892* (2021.01); *A61M 2039/244* (2013.01); *A61M 2039/248* (2013.01)

(58) Field of Classification Search
CPC ........ A60M 1/562; A60M 1/40; A60M 1/892; A60M 1/268; A60M 1/284
See application file for complete search history.

(56) References Cited

U.S. PATENT DOCUMENTS

| | | | | |
|---|---|---|---|---|
| 4,080,958 | A * | 3/1978 | Bregman | A61M 60/40 600/16 |
| 4,240,409 | A * | 12/1980 | Robinson | A61M 60/40 600/16 |
| 4,552,552 | A * | 11/1985 | Polaschegg | A61M 1/302 604/9 |
| 4,782,817 | A | 11/1988 | Singh et al. | |
| 4,906,229 | A | 3/1990 | Wampler | |
| 6,030,335 | A * | 2/2000 | Franchi | A61M 60/268 600/16 |
| 9,234,514 | B2 * | 1/2016 | Jones | A61M 60/113 |
| 2006/0236756 | A1 | 10/2006 | Rinaldi et al. | |
| 2010/0192686 | A1 * | 8/2010 | Kamen | G06F 11/30 715/764 |
| 2011/0282126 | A1 * | 11/2011 | Nour | A61M 60/274 600/16 |
| 2013/0035628 | A1 * | 2/2013 | Garrison | A61M 60/268 604/8 |
| 2017/0130707 | A1 * | 5/2017 | Tournebize | F04B 49/08 |

FOREIGN PATENT DOCUMENTS

| | | |
|---|---|---|
| WO | 0035515 | 6/2000 |
| WO | 2010066899 A1 | 6/2010 |
| WO | 2010073890 A1 | 7/2010 |
| WO | 2011117566 A1 | 9/2011 |
| WO | 2013022796 A2 | 2/2013 |

OTHER PUBLICATIONS

Search Report under Section 17 dated Feb. 20, 2017 from counterpart GB Application No. 1615650.7 6 pp.
International Search Report and Written Opinion dated Dec. 1, 2017 from counterpart international application ho. PCT/GB2017/052706, 15 pp.

* cited by examiner

BLOOD PUMP

This application is a national stage entry under 35 U.S.C. § 371 of International Application No. PCT/GB2017/052706, filed Sep. 14, 2017, which claims the benefit of GB Application No. 1615650.7, filed Sep. 14, 2016. The entire contents of International Application No. PCT/GB2017/052706 and GB Application No. 1615650.7 are incorporated herein by reference.

TECHNICAL FIELD

The present disclosure relates to a blood pump apparatus, in particular for use in Extracorporeal Life Support (ECLS) systems.

BACKGROUND

Currently, ECLS is supported by bulky bedside equipment with tubing carrying the blood flow from a catheter to the bedside and more tubing carrying the oxygenated blood back to the patient via an oxygenator. A pump withdraws blood through the extraction catheter and pumps it through the oxygenator from where it returns to the body through the return catheter. Where pumps that are not positive displacement are employed, the circuit also contains a blood flow meter which provides feedback to control the blood flow rate. Gas/fluid mass exchange apparatuses are commonly used in medical practice for transferring oxygen from air to a blood supply and carbon dioxide from blood to the air. Such devices are typically referred to as oxygenators and most frequently employ pure oxygen as the gas phase. The bedside equipment arrangement limits patient mobility and hampers access to the patient. A lack of mobility causes a general deterioration in patient condition (although not as extreme as resulting from mechanical ventilation). The long blood lines joining the patient and the bedside equipment also present a vulnerability that requires extra vigilance on the part of medical staff and any visitors to the bedside. A major reason why bulky bedside equipment is required is that the blood flow needs to be connected to an electrically driven pump, most often a centrifugal or peristaltic pump.

SUMMARY

The present disclosure seeks to improve existing devices for blood pumping, in particular in an ECLS system.

According to a first aspect of the present disclosure there is provided a blood pump apparatus arranged to provide pulsatile flow, the apparatus comprising a flexible inner cylindrical duct providing a blood flow region, and an outer cylindrical duct arranged to surround the inner cylindrical duct and arranged to accommodate a pumping fluid, the inner cylindrical duct having a blood inlet for receiving blood into the region, a blood outlet for passing blood out from the blood flow region and a passageway therebetween, the inner duct further comprising a non return valve at the blood inlet and a non return valve at the blood outlet, the outer cylindrical duct having a fluid port for a pumping fluid, and a pump device arranged to cyclically deliver and withdraw pumping fluid to the fluid port thereby cyclically compressing and expanding the flexible inner cylindrical duct urging blood through the blood flow region and delivering a pulsating blood flow through the blood outlet.

The tubing in a typical adult ECMO circuit contains between 200 ml and 400 ml. For an adult (weighing 70 kg or 11 stone), each heart beat delivers about 100 ml. The pump described below delivers a very similar stroke volume to be synchronized with the heart, and can be fitted neatly into the existing tubing. The average volume of blood in the pump can be around half of the volume in a ECLS system without this pump, providing a further benefit of reducing the volume of blood outside the body. Advantageously, by the use of the tubing that is already employed in ECMO/ECLS as a pump, there is, in effect the elimination of one piece of equipment from the blood circuit.

The existing systems such as described in PCT/GB2011/00354 utilise one of two pump types: (1) A peristaltic pump with an in expensive replaceable part, consisting of a length of plastic tube, but with the disadvantage that the roller action on the blood within the tube causing the peristaltic flow crushes a proportion of the red blood cells causing haemolysis with consequent adverse effects on the patient's health. (2) A centrifugal pump with a replaceable part comprising a polymeric pump head which contains an impeller that is externally magnetically driven. The impeller may be supported on low-friction, non-lubricated bearings, or may be magnetically levitated. The rapid rotation of the impeller causes some haemolysis, although less than that from a peristaltic pump. Both of these prior art pumps share two common disadvantages. The first disadvantage is that the flow produced is steady—a sustained steady blood flow through the mammalian body results in damage and is undesirable. This disadvantage is manifest even in the relatively short periods (less than 6 hours) of a cardiopulmonary bypass procedure. The second disadvantage is that the replaceable blood-contacting parts must be near to the driving mechanism. Thus, both must be connected to relatively bulky drivers which include electrical connections to the respective motors. This limitation restricts where the pump sits in the ECLS circuit to normally being on a bedside table or trolley. It is not readily practicable to place a pump on a patient, which is the best position to minimize the length of tubing and to deliver patient mobility. Centrifugal and turbine pumps are known and used as ventricular assist devices. These pumps are designed to be extremely compact with the whole pump disposable when it needs to be replaced.

Advantageously, this blood pump provides an improvement for ECLS systems as the pump is separated from its electrical drive unit, and can therefore be placed anywhere in the ECLS circuit and the long blood lines to and from the bedside can be eliminated. Furthermore, with the blood pump becoming part of the tubing, it effectively removes a bulky item from the blood circuit and removes the necessity for tubing containing blood to be connected to the bedside (since the blood pump and the oxygenator may be placed on the patient, rather than at the bedside). In this way, access to the patient and patient mobility is greatly improved. Such improved mobility would accelerate patient recovery with benefit both to the patient and to the health care provider; there would be reduced hospital stays and reduced requirement for expensive high dependency and intensive care beds. Prolonged periods spent with patients immobile in intensive treatment facilities result in deterioration in muscle tone and other changes that reduce recovery rates and greatly extend hospital stays A further benefit of the innovation is delivery of a pulsating blood flow, preferably having a controlled pulse profile. CPB studies have shown that, the steady blood flow and prolonged steady flows provided by currently used blood pumps results in deterioration of blood health with consequent long-term adverse effects on patient health. Known risks of steady flow include acquired Von Willebrand disease (resulting in haemorrhage), thrombosis, aortic valve insufficiency, and diffuse nerve cell changes in the brain (possibly accounting for "pump head", the confused condition experienced by a number of patients subjected to ECLS). A non-pulsatile flow also gives a greater risk of blood clots forming in the ECLS circuit; pulses tend to dislodge clots before they have a chance to grow.

Blood clotting processes progresses when blood leaves the blood vessels and travels over a foreign surface, such as a mass exchanger surface, or within the ECLS tubing. The longer the blood is out of the blood vessels, the greater the risk and extent of blood clotting. It follows that the longer the residence time of blood out of the blood vessels, the greater is the risk that harmful clots will be returned to the body, with both detrimental impact on a patient's health and risk that a clot will cause death. As part of the clotting process, the apparent viscosity of the blood increases, and the longer the blood is out of the body, the further this thickening process proceeds. This thickening has a detrimental impact on mass exchanger performance because increasing viscosity decreases the diffusivities of oxygen and carbon dioxide in the blood. There are therefore strong incentives to minimize the total volume of blood outside the body and the time blood spends in such an apparatus. Additionally, there is particular benefit for paediatric patients in having less blood outside the body.

Preferably, the flexible inner duct is elastic, more preferably, the outer cylindrical duct comprises a substantially fixed diameter tube and can be flexible. The outer duct or tube cannot be kinked so avoiding compromising the blood flow. The blood flows though the inner duct or tube and the flexible outer tube advantageously allows the delivery of an oscillating flow to a pumping fluid, resulting in the pump delivering a pulsating blood flow. By employing an elastic tube within a flexible but inelastic tube the pump arrived at is such that the volume within the elastic tube can be cycled by a remote activator connected only by a tube conducting a pumping liquid. In this way, the replaceable part of the pump is lightweight and can be placed anywhere within a CPB or ECLS circuit—it is not restricted to a bedside table or trolley, and is preferably placed on the patient's body. Advantageously, the blood-contacting and replaceable part is inexpensive, consisting as it does of two concentric tubes with a non-return valve at each end.

In an embodiment the one or more non return valve is one selected from the range of; floating ball valve, shaped-float valve, unsprung poppet valve, flap valve, valve with shaped flap, hydraulic or pneumatic actuated non-return valve, cyclone-type fluidic rectifier.

In the case of a hydraulically operated valve that, for example, operates by gently squeezing the tubing, the valve may be driven by the same liquid as used to provide the pumping action. For example, if the pumping liquid is driven back and forth by a piston driven from a cam, the valve(s) may be operated from separate cams on the same camshaft. In this way, they may remain synchronized when the pumping frequency is changed. The driving unit may then advantageously be connected to the replaceable pump head by a two or three lumen tube.

In an embodiment the pump device generating cyclic flow is one of the range of piston and cylinder driven by a crankshaft, variable lift cam, electronically, bellows driven by a crankshaft, variable lift cam, or electronically (that is, the moving part (piston or bellows) may be driven by a crankshaft, by a cam, or electronically by a linear motor). The range of pumping devices is advantageous to the flexibility of the system. As the pumping fluid can be driven by a piston, or bellows, it can provide an oscillating flow to give any desired flow profile. The piston can be driven by a crankshaft, by a cam, or directly by a linear motor.

The cam or electronic versions are favoured because a cam can be profiled to produce a pulse profile similar to that of the natural heart, and electromechanical devices can also be programmed to produce a pulse profile similar to that of the heart. It has been shown that, for most benefit, the pulse profile should match that of the natural heart.

The pump is a positive displacement pump, that is, it may deliver a defined flow rate without use of a separate flow meter and feedback control unit. Thus, with an outer tube of fixed volume, the volume of blood pumped at each stroke is equal to the volume of pumping fluid discharged from the cylinder, or bellows, at each stroke which, in turn is determined by the geometry of the cylinder. The volume of each stroke can optionally be adjusted by, for example, employing a variable lift cam. The activating mechanism can be remote from the pump with just a narrow tube containing pumping fluid connecting to the pump. In a variant, the pumping fluid can be sealed in a bladder where it fits into the cylinder or bellows of the activating mechanism.

In an embodiment, the pumping fluid is any one selected from the range of saline, a blood compatible aqueous solution, water, silicone oil.

In an embodiment, the blood pump apparatus is adapted to be placed on a human body undergoing treatment or life support. In an embodiment the pump apparatus is disposable after each use.

Typically, the blood pump further comprises a delivery tube arranged to deliver blood to the blood inlet and/or a receiving tube arranged to receive blood from the blood outlet, wherein at least one of the delivery tube and the receiving tube comprises at least one resiliently-deformable section. The resiliently-deformable section typically helps to provide a degree of smoothing of the pulsing blood flow generated by the blood pump, such that the blood flow is a closer approximation of that found in natural circulation.

Other variants can feature in an embodiment to provide the flow required for an individual situation or patient, for example there may be a plurality of inner and outer ducts in series in the blood pump apparatus.

Advantageously, as set out above the blood pump is arranged as an integral part of an Extracorporeal Life Support (ECLS) system or an Extracorporeal Membrane Oxygenation (ECMO) system. The robust nature of the pump combined with its flexibility enables it to be placed anywhere in an ECLS circuit, including on the patient.

In certain embodiments, two blood pumps may be provided that operate side-by-side and discharge the pumped fluid (e.g. blood) into a single tube. The two pumps typically operate out of phase (for example, out of phase by 180°), so as to provide a flow profile that is intermediate between continuous flow and sharply pulsatile flow.

BRIEF DESCRIPTION OF THE DRAWINGS

Embodiments of the present disclosure will now be described by way of example only and with reference to the accompanying drawings.

DETAILED DESCRIPTION

Figure 1:
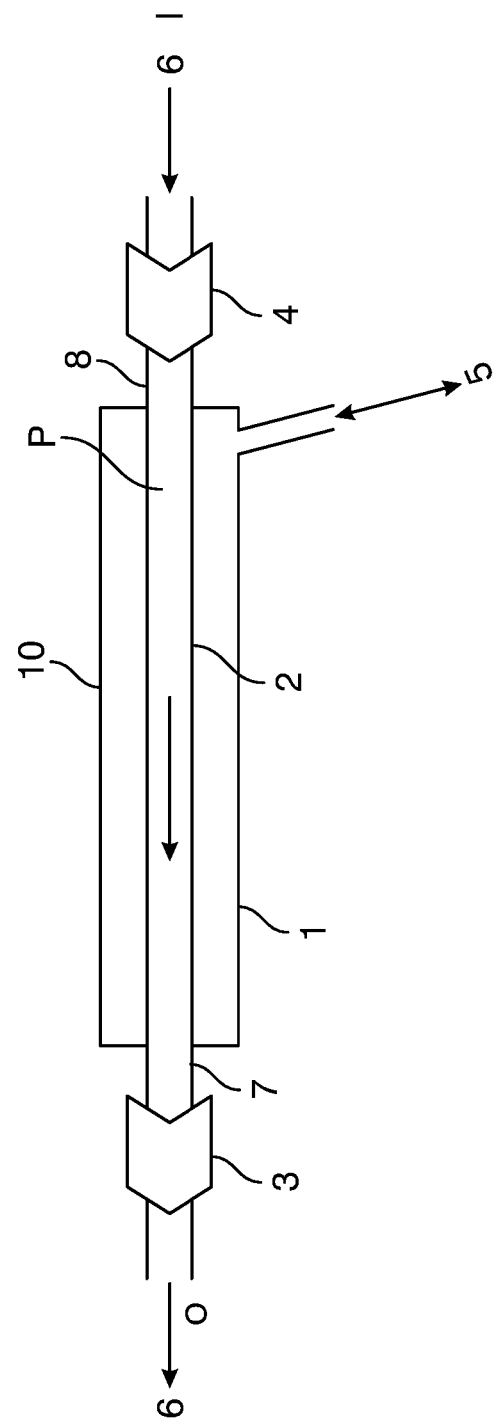
FIG. 1 is a cross-sectional schematic view of a pump apparatus according to an embodiment of the present disclosure.

Referring to FIG. 1 of the drawings, there is illustrated a pump apparatus 1 according to a first embodiment of the present disclosure for providing pulsatile flow, the apparatus 1 comprising a flexible inner cylindrical duct 2 providing a blood flow region, and an outer cylindrical duct 10 arranged to surround an enclose the inner cylindrical duct 2 and arranged to accommodate a pumping fluid 5. The outer duct 10 comprises a tube of greater diameter than the inner duct 2 and is less elastic than duct 2, and being designed not to kink or deform. The inner cylindrical duct 2 comprises a blood inlet, I, for receiving blood 6 into the region, a blood outlet, O, for passing blood 6 out from the blood flow region and a passageway P therebetween. The inner duct 2 comprises extension ends 7, 8, which include fitted which non-return valves; valve 3, at the outlet O, and valve 4, at the inlet, I. The extension ends 7, 8, are non-elastic. The outer cylindrical duct 10 has a fluid port 5, for a pumping fluid, and a pump device (not shown) arranged to cyclically deliver and withdraw pumping fluid to the fluid port 5. The inner cylindrical duct 2 and the outer cylindrical duct 10 are sealed together at each end. By this arrangement the pump device thereby cyclically compresses and expands the flexible inner cylindrical duct 2 urging blood through the blood flow region and delivering a pulsating blood flow 6 through the blood outlet, O. The pumping fluid in the illustrated embodiment is saline, and the volume between the outer duct 10, and the inner duct 2 is filled with the saline.

The non-return valves can optionally be replaced with unequal resistance valves so that there is a greater resistance to flow in one direction than the other. However, non-return valves are preferred to unequal resistance valves (otherwise known as fluid rectifiers), because non-return valves help to maintain the positive displacement characteristics of the blood pump.

The volume between the tubes is filled with a pumping liquid (5) which is pumped cyclically in and out of the space.

Figure 2:
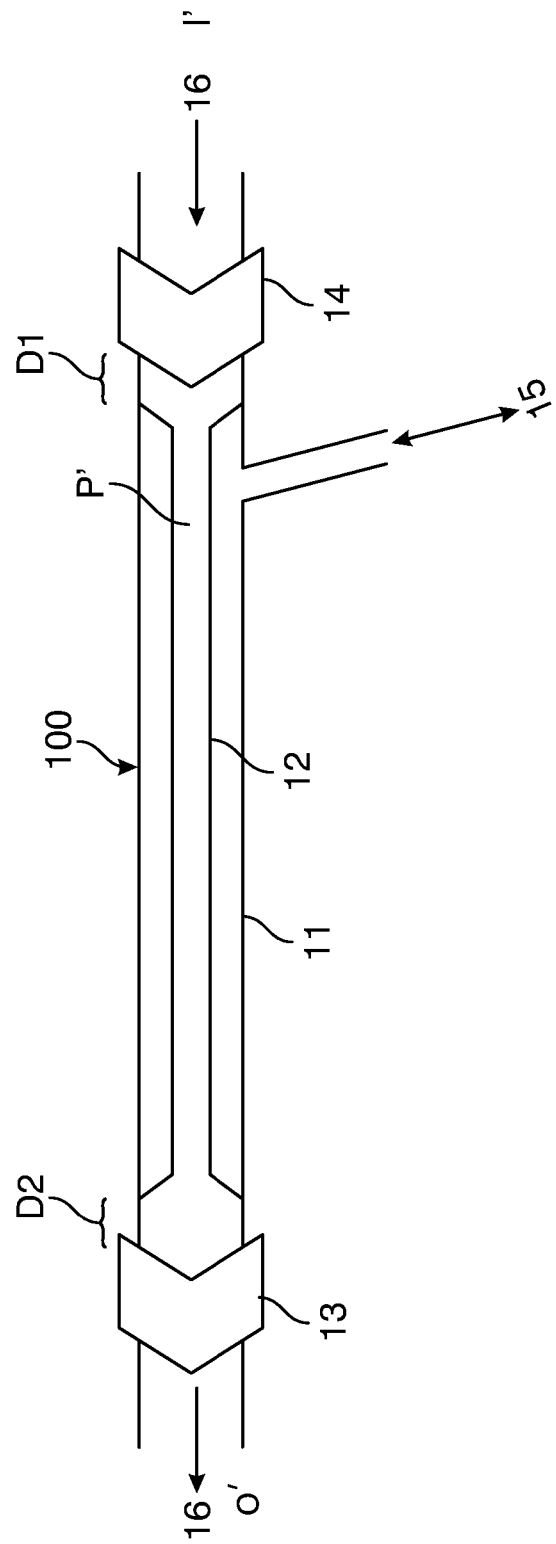
FIG. 2 is a cross-sectional schematic view of a pump apparatus according to an alternative embodiment of the present disclosure.

Turning now to FIG. 2 of the drawings, an alternative embodiment of the disclosure will now be described. The pump 100, is similar to the pump 1 of FIG. 1, it consists of a blood-compatible elastic inner duct section 12 enclosed in a less elastic duct or tube 11 of greater diameter. The outer duct 11 or tube is designed to maintain its diameter and not to kink or deform. The inner section 12 is sealed to the outer duct or tube 11 at each end. The inner cylindrical duct 2 comprises a blood inlet, I', for receiving blood 16 into the blood flow region, a blood outlet, O', for passing blood 16 out from the blood flow region and a passageway P' therebetween.

The inner duct 12 comprises end portions D1, D2 exhibiting a gentle change in diameter from one region to the other. The end portions D1, D2 are arranged such that blood flow 16 in the outer duct or tube 11 is delivered to the inner section 12 through a gentle change in diameter (region D1) where the section joins the outer tube 11. Similarly, the inner section delivers blood to the outer section through a gentle change in diameter (region D1) where it joins the outer tube 11. D1 and D2 further comprise non-return valves; downstream valve 13, at the outlet O', and upstream valve 14, at the inlet, I', and each end of the outer tube or duct features the fitted valves 13, 14.

The outer cylindrical duct 11 has a fluid port 15, for a pumping fluid, and a pump device (not shown) arranged to cyclically deliver and withdraw pumping fluid to the fluid port 15. In a variation of the second embodiment the non return valves 13, 14 can be replaced with unequal resistance valves so that there is a greater resistance to flow in one direction than the other.

As shown in FIG. 1, the volume between the tubes or ducts is filled with a pumping liquid which is pumped cyclically in and out of the space so as to cause blood, 16, to be pumped through the body of the pump.

Also, as for the embodiment of FIG. 1, the pumping liquid can be any suitable non-toxic liquid such as saline solution, water or silicone oil.

As for the first embodiment, two pump bodies can be placed in parallel so that a pulsating flow can be achieved without an extended zero flow period in each cycle.

For CPB applications, the stroke volume is typically 0.6 ml to 1.2 ml per kg of body weight with an adjustable cycle time of one cycle per second. The stroke volume is the volume of saline pumped into and out of the space between the inner and outer tubes at each cycle. The change of volume of the elastic section from fully expanded to fully collapsed must be greater than the stroke volume.

In operation and in use the apparatus of FIG. 1 and FIG. 2 function as follows; the saline solution cyclically fills and empties the space between the ducts 2, 12, 10, 11 or tubes. As saline (entry point at 5) is drawn from the volume between the ducts 2, 12, 10, 11 or tubes, the elastic inner duct 2, 12 expands and draws blood (6, 16) in from the blood inlet valve 4, 14. The non-return valve 3, 13 at the outlet O, O' stops blood being drawn in from the outlet O, O'. At the end of the pumping stroke, the saline (from 5, 15) is forced back into the volume between the ducts or tubes 2, 12, 10, 11. As the saline flows into the space, it forces the elastic inner duct or tube 2, 12 to contract which, in turn, forces the blood 6, 16 out through the outlet valve 3, 13. The non-return valve 4, 14 at the inlet I, I' stops blood flowing back to the inlet I, I'. Thus, as saline flows cyclically back and forth, the blood is drawn into the inlet I, I' and pumped out of the outlet O, O" in a pulsating manner (from right to left as illustrated in FIG. 1). Where the outer duct or tube 10, 11 retains its volume during the pumping cycle, the pump 1, 100 closely approximates a metering pump.

It is not necessary (or desirable) for the surfaces of the inner duct 2, 12 to touch when the saline is forced into the space between the outer duct 10, 100 and the elastic inner duct 2, 12. Whilst the inlet valve is closed, the stroke volume is pumped out through the exit valve whether or not the elastic tube is forced to fill the inner space. This flexibility has two benefits. First, by ensuring the surfaces do not touch the blood is not squeezed and damage is minimized. Secondly, since the pump always delivers the stroke volume independent of the volume of blood in the device, the same pump head can be used with varying stroke volumes to give higher or lower flows.

In this embodiment the whole of the pump illustrated in FIG. 1 and FIG. 2 is disposable after each use.

In both embodiments the cyclic flow of saline (5) can be generated by a cylinder, a bellows, or a membrane. Where the cyclic flow is generated by a piston and cylinder, the piston movement can be achieved by rotating crank wheel and crankshaft, or by a rotating cam profiled to give the flow pattern desired. The piston can also be directly driven electromagnetically. Where the cyclic flow is driven by a bellows, the bellows can be opened and closed by any of the means noted for the piston.

The saline may also be enclosed by a volume retained within a vessel bounded by a flexible non-porous membrane. The membrane is then flexed by any of the means noted for the piston.

The saline may be introduced into the cyclic pumping mechanism when the pump is set up. Alternatively, the saline shown as entering the pump in FIG. 1 and FIG. 2 may be sealed into a tube ending in a bladder that becomes an integral part of the disposable pump. The bladder is then placed into the piston and cylinder, the bellows, or the volume whose size is adjusted by movement of a membrane.

The non-return valves may be of similar design to any of those used as artificial heart valves. The valves for this pump can be simpler and less expensive than heart valves because the service requirement is less stringent. It is less stringent because the flow/pressure profile is controlled mechanically, so that, on opening and closing, the blood is less stressed than in a natural heart. It is also less stringent because the projected life of the valve is less, and it is less stringent because the valve and pump are more readily replaced. Alternatively, a fluidic rectifier with no moving parts may be employed. For example, a cyclone rectifier may be employed. The cyclone has two entrances, one is tangential at the outer diameter, the other is axial. When fluid is fed into the tangential inlet, the angular velocity increases as the liquid moves towards the axis thus creating higher g-forces and a higher pressure drop. When fluid is fed into the axial entrance, the non-rotating flow does not create an increased pressure drop. Hence, a cyclone rectifier can be fitted as valve 3 in FIG. 1 with the axial entrance towards the pump and as valve 4 with the tangential axis towards the pump. When saline is forced into the space between tubes 1 and 2, there will be a lower resistance to flow through valve 3 than valve 4, so that there will be a net flow from left to right. Conversely, when saline is withdrawn from the space between tubes 1 and 2, there is a greater pressure drop through valve 3 than valve 4. Hence, again there is a net flow from left to right.

Improved control of flow can be achieved with two pumps (each similar to that of FIG. 1) in parallel and working 180 degrees out of phase. The advantage of this arrangement is that there need be no zero flow either in or out. By, for example, arranging suitable cam profiles, the flow can pulsate from zero to a maximum, or from a low flow rate to a maximum. This parallel arrangement is particularly favourable for the fluidic valve option. The fluidic valve has a proportion of back flow throughout the cycle. Such a back flow has a deleterious impact on the mammalian circulation. By having two pump bodies in parallel, the forward flow from one pump body can match or exceed the backward flow from the other pump body throughout the pumping cycle.

Figure 3:
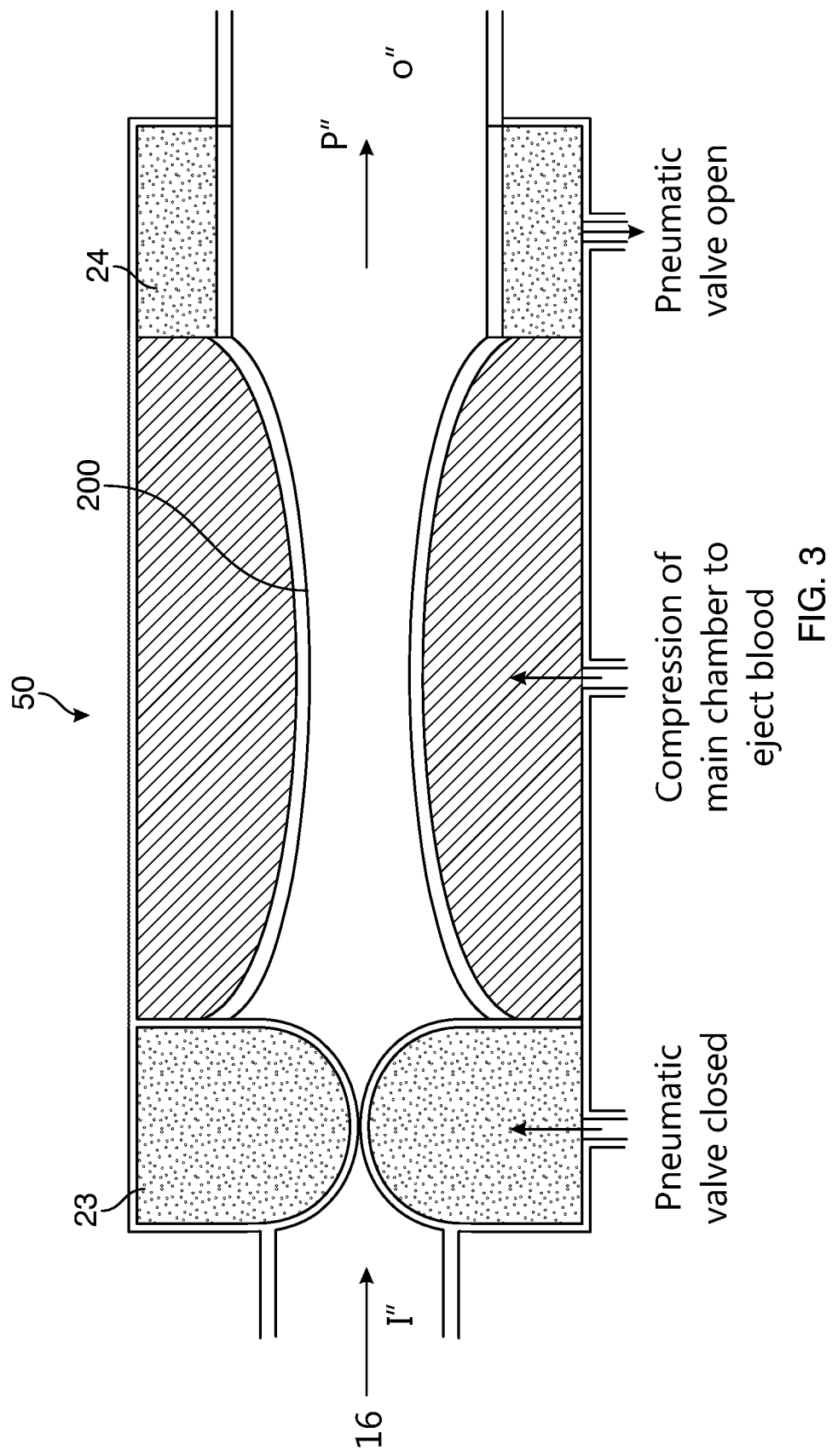
FIG. 3 is a is a cross-sectional schematic view of a pump apparatus according to a further alternative embodiment of the present disclosure.

FIG. 3 shows a cross-sectional schematic view of a pump apparatus 50 according to a further alternative embodiment of the present disclosure, the layout and operation of which will now be described.

The flexible inner tube or duct 200 is such that, as for the embodiments, illustrated in FIG. 1 and FIG. 2 pneumatic compression can be achieved with a pumping fluid 25 so as to cause the ejection of blood from the inner duct 200. The pump comprises a blood inlet, I", for receiving blood 16 into the blood flow region, a blood outlet, O", for passing blood 16 out from the blood flow region and a passageway P''' therebetween. In FIG. 3 the valves are illustrated as comprising a pneumatic function too. FIG. 3 shows that the inlet valve 23 is closed by fluid flowing into it and the inner duct or tube 200 is then compressed as fluid is 'sucked' out of an exit in the valve 24 which is, therefore, open. The outlet valve 24 is then closed by fluid flowing into it, the inlet valve 23 is opened and the main chamber passageway P is then depressurised to allow blood to be drawn in before the sequence is repeated.

Figure 4:
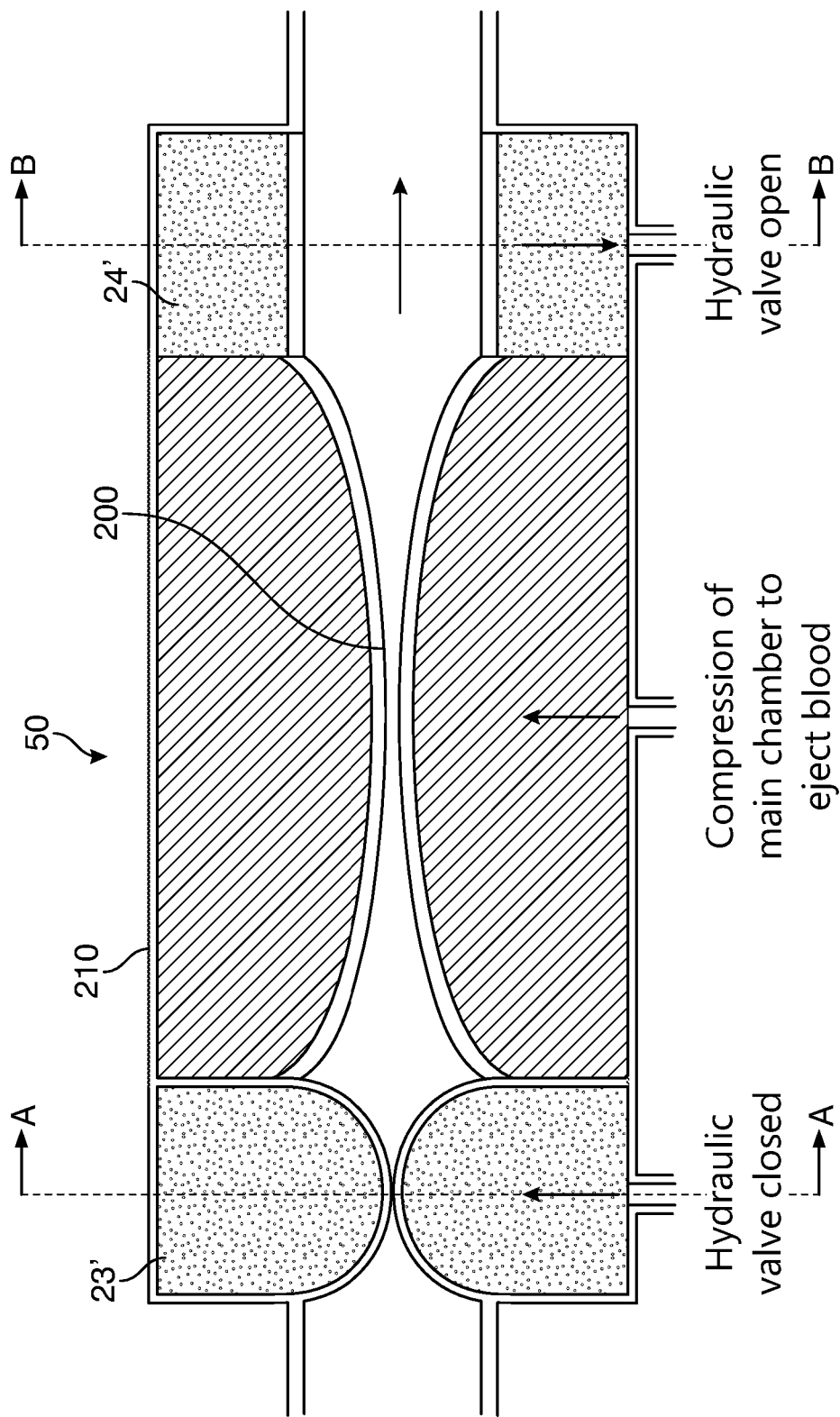
FIG. 4 is a cross-sectional schematic view of a modification of the embodiment shown in FIG. 3.

FIG. 4 shows a modified version of the blood pump apparatus of FIG. 3, in which the pneumatic valves 23, 24 of FIG. 3 are replaced by corresponding hydraulic valves 23' and 24'.

Each of hydraulic valves 23', 24' is supplied by a respective liquid drive, the outer duct 210 also being supplied by its respective liquid drive. The three liquid drives may be operated from separate cams on the same camshaft.

Figure 5:
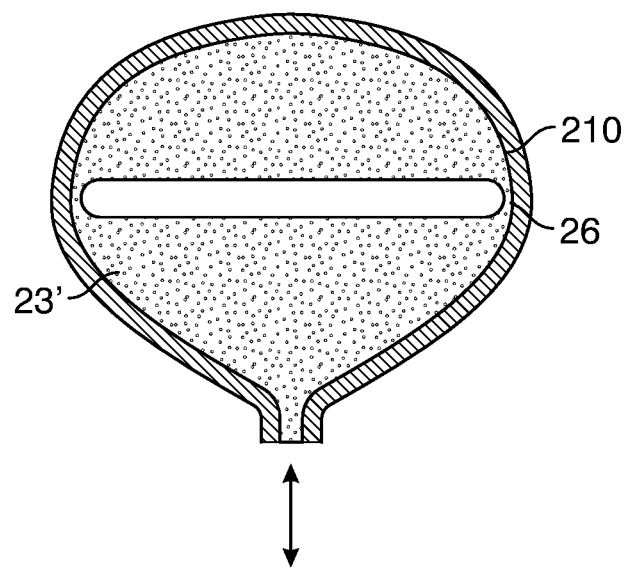
FIG. 5 is a cross-sectional view taken along the line A-A of a version of the embodiment shown in FIG. 4.
Figure 6:
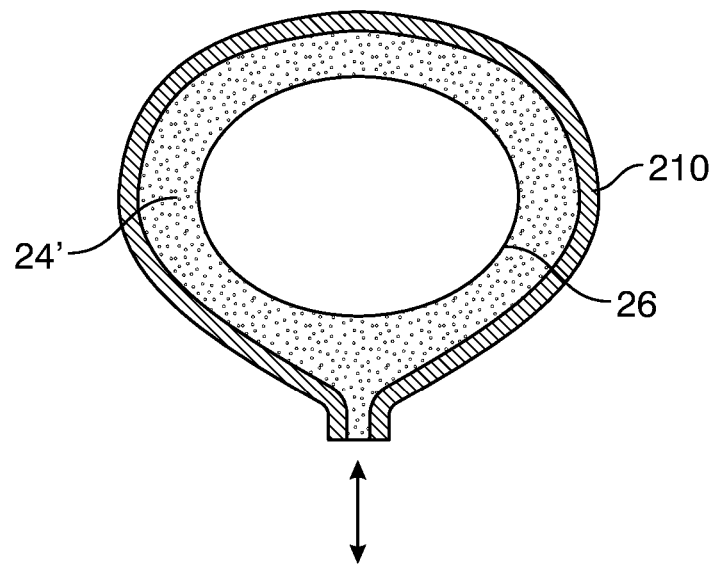
FIG. 6 is a cross-sectional view taken along the line B-B of a version of the embodiment shown in FIG. 4.

The hydraulic valves 23', 24' are typically membrane valves. For example, as shown in FIG. 6, the membrane 26 may be pulled back against the inner circumference of the duct 210 when the valve is open (thus defining a circular opening). When the valve is closing (as shown in FIG. 5), the membrane 26 may expand towards the centre of the duct, initially leaving an elliptical aperture, which ultimately closes along a line.

Figure 7:
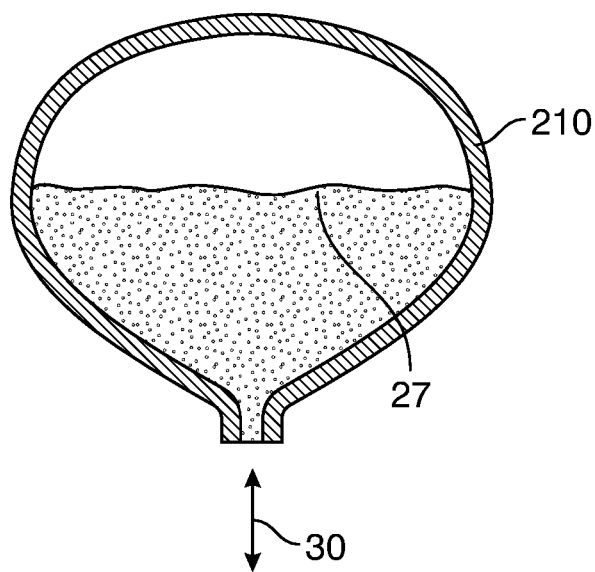
FIG. 7 is a cross-sectional view of an alternative valve configuration for use in embodiments of the present disclosure.

Alternatively, as shown in FIG. 7, the membrane 27 may rest against one arc of the duct circumference when the valve is open and may expand towards the opposite side of the duct circumference when the valve is closing. That is, when the pumping fluid is withdrawing through opening 30, the membrane drops to the bottom of the duct, thereby leaving the duct open for the flow of blood. When pumping fluid is forced in through the opening 30, the membrane extends towards the top of the duct, thereby closing the valve.

It is not necessary for the inlet and outlet valves to be of the same type. For example, one could be a hydraulic valve and the other a poppet valve.

We note that FIGS. 3 and 4, in particular, show schematic views of embodiments of the disclosure. In particular, the relative size of the valves in FIGS. 3 and 4 is exaggerated, to clarify their operation. In practice, the internal profile of the pump is much smoother than shown in FIGS. 3 and 4.

Advantages of the blood pump described are set out above and to reiterate, stem from the fact that the pump is not connected directly to an electric motor so that it is much lighter than competitive pumps, which gives flexibility as to where it may be fitted, including the option of placing it on the patient's body. If worn, the electric motor driving the piston (or alternative means of pumping the saline) can be at any convenient place—it is not restricted to a place adjacent to the ECLS circuit. In addition the pump delivers a pulsating flow and the flow profile can be adjusted (for example, by suitable definition of cam profile or electromechanical drive) to give the best biocompatible match, for example, to match a profile as produced by the natural heart. The pulsating flow is physiologically beneficial and an improvement over a steady state flow. As the pump body consists of a flexible tube, this means that it can form part of the tubing for an ECLS circuit with consequent reduction in total priming volume of the circuit.

Various modifications may be made to the described embodiments without departing from the scope of the present disclosure. It is also envisaged to include the mass exchanger (oxygenator) in the tubing. In this design then a connection from the blood pump active tubing to the patient could be made without any bedside kit (apart from the services, saline and oxygen) needed to drive the pump and oxygenator.

Other valves could be a floating ball valve for example. This type of valve and its derivatives have a lightweight free-floating component held in a cage downstream of the flow. In forward flow, the component (ball) lifts off the seat and is restrained by the cage not to float off with the flow. When the flow reverses the component floats back to sit on the seat that seals the flow. There would seem to be advantages in a ball in that it will rotate somewhat so that it does not always sit in the same place, which seems to have advantages in minimizing sites on which clots might grow. A shaped float may also be used instead of a ball in order to provide a gentle closure, but with the difficulty that it cannot rotate.

A flap valve is tethered on one side, and does not need to be caged. The flap itself can be flat, or any shape that fits neatly into a seating. The most successful heart valves are of this type and a specifically designed hinge, can be made to effect a gentle but firm closing. The hinge will have a gentle closing action so that the valve can be operated in any orientation.

A poppet valve is held upstream of the valve seating. Traditionally, these are closed by springs, but in the present disclosure it could float. In the forward direction, the head would float off the seat in the downstream direction of flow leaving it open, whilst a cross-piece on the upstream end of the valve shaft would come against a seat on the upstream side of the valve. The cross-piece would not seal the whole area so that blood would flow freely. In the reverse flow direction, the valve head would float back onto its seating and seal the flow. Options include magnetically levitating the valve to minimize scope for causing haemolysis and clotting.

If the valve is actuated hydraulically or pneumatically, the inner tube is in effect squeezed gently to close, a sleeve valve of another valve types could be used.

A fluidic rectifier has the advantage of no moving parts, so therefore should not promote haemolysis or clotting.

The body and ducts may be of an alternative shaping and may comprise any suitable material and may be of varying length and thickness. Alternative forms of construction and features may be considered. The shape of the ducts may be of any shape to conform to the available space and so as to be ergonomically designed to fit to the patient or to include other functional features. The inlet and outlets may be a suitable size in order to combine and fit with existing systems. The ducts may comprise plastic, injection moulded material or other task specific or site specific material. They may include sterilised components.

The shape of the valves and/or ducts may also be selected so as to limit stasis of the blood being pumped and/or reduce the risks of recirculation or reverse flow.

The invention claimed is:

1. A blood pump system, the system comprising:
   a delivery tube;
   a receiving tube; and
   an extracorporeal positive displacement blood pump comprising:
      a first non-return valve;
      a second non-return valve;
      a flexible inner duct providing a blood flow region between the first non-return valve and the second non-return valve,
      an outer duct arranged to surround the flexible inner duct and arranged to accommodate a pumping liquid, the flexible inner duct having a blood inlet for receiving blood from the delivery tube through the first non-return value into the blood flow region, a blood outlet for passing blood out from the blood flow region through the second non-return valve to the receiving tube, the outer duct being a fixed volume and having a liquid port for the pumping liquid, and
      a pump device comprising a piston driven within a piston cylinder, the pump device configured to:
         cyclically deliver and withdraw a controlled volume of pumping liquid to the liquid port by the piston, to cyclically compress and expand the flexible inner duct to urge an equal controlled volume of blood through the blood flow region and to deliver a pulsating blood flow through the blood outlet, the pulsating blood flow having a controlled pulse profile;
         wherein to urge the volume of blood through the blood flow region, the piston is configured to withdraw the volume of pumping liquid from the liquid port when the first non-return valve is open and the second non-return valve is closed, and to deliver the volume of pumping liquid to the liquid port when the first non-return valve is closed and the second non-return valve is open, and
         wherein movement of the piston within the piston cylinder is further configured to control the volume of pumping liquid delivered to the liquid port to vary the volume of blood urged through the blood flow region and to control the pulse profile.

2. The system of claim 1, wherein the flexible inner duct is elastic.

3. The system of claim 1, wherein the outer duct comprises a substantially fixed diameter tube.

4. The system of claim 2, wherein the inner duct is of circular cross-section when fully expanded.

5. The system of claim 1, wherein the pumping liquid comprises one of saline, a blood compatible aqueous solution, water, or silicone oil.

6. The system of claim 1, wherein the system is adapted to be placed on a human body undergoing treatment or life support.

7. The system of claim 1, comprising a plurality of inner and outer ducts in series in the blood pump device.

8. The system of claim 1, wherein at least some blood contacting parts of the system are disposable after use.

9. The system of claim 1, wherein the system comprises an Extracorporeal Life Support (ECLS) system or an Extracorporeal Membrane Oxygenation (ECMO) system.

10. A system comprising:
    two or more blood pump apparatuses in parallel, each blood pump apparatus comprising a blood pump system according to claim 1.

11. The system of claim 1, wherein the system is configured to:
    deliver a defined flow rate; and
    to adjust the defined flow rate, adjust one or both of the volume of the pumping liquid cyclically delivered and withdrawn to the liquid port or a pumping frequency at which the pump device cyclically delivers and withdraws the volume of pumping liquid to the liquid port.

12. The system of claim 1, wherein the pump device comprises a moving part configured to deliver an adjustable volume of the pumping liquid to the liquid port to adjust the volume of blood urged through the blood flow region.

13. The system of claim 1, wherein the extracorporeal positive displacement blood pump is configured to deliver a defined flow rate without use of a separate flow meter or feedback control unit.

14. The system of claim 1, wherein the pump device is configured to cyclically deliver and withdraw the volume of pumping liquid to the liquid port to cyclically compress and expand the flexible inner duct to urge the volume of blood through the blood flow region and to deliver the pulsating blood flow with a controlled pulse profile through the blood outlet.

15. The system of claim 1, further comprising a sealed bladder provided in the piston cylinder, the sealed bladder configured to contain the pumping liquid.

* * * * *